United States Patent
Behringer (12)

(10) Patent No.: US 6,344,565 B1
(45) Date of Patent: Feb. 5, 2002

(54) PREPARATION OF CYCLOACID

(75) Inventor: Klaus Behringer, Basel (CH)

(73) Assignee: Roche Vitamins, Inc., Parsippany, NJ (US)

( * ) Notice: Subject to any disclaimer, the term of this patent is extended or adjusted under 35 U.S.C. 154(b) by 0 days.

(21) Appl. No.: 09/643,273

(22) Filed: Aug. 22, 2000

(30) Foreign Application Priority Data

Aug. 27, 1999 (EP) ............................................. 99116967

(51) Int. Cl.$^7$ ............................................. C01D 233/30
(52) U.S. Cl. .................................................. 548/322.5
(58) Field of Search ...................................... 548/322.5

(56) References Cited

U.S. PATENT DOCUMENTS

| 5,151,525 A | 9/1992 | Seiter |
| 5,763,469 A | 6/1998 | Delucca |

FOREIGN PATENT DOCUMENTS

| DE | 3440 141 A1 | 5/1986 |

OTHER PUBLICATIONS

Derwent English language abstract of DE 3440 141 A1 (document B1) 1986.
De Clercq, "Biotin: A Timeless Challenge for Total Synthesis," *Chem. Rev.*, vol. 97, pp. 1755–1792 (1997).
Eckert, et al., "Triphosgen, Ein Kristalliner Phosgen–Ersatz," *Angew. Chem.*, vol. 99, No. 9, pp. 922–923 (1987).
Cortez, et al., "Synthesis of Quinazolinedione Using Triphosgene," *Synthetic Communications,*, vol. 21(2), pp. 285–292 (1991).
Jong–Man, et al., "Synthesis of a Cyclic Urea as a Nonnatural Biopolymer Scaffold," *Tetrahedron Letters*, vol. 37, No. 30, pp. 5309–5312 (1996).
Ishiii, et al., "Enantioselective Methylation of the Lithium Enolate of 1–Tetralone Mediated by Chiral $C_2$–Symmetric DMEU Derivatives," *Tetrahedron Letters*, vol. 38, No.4, pp. 563–566 (1997).

*Primary Examiner*—Joseph K. McKane
*Assistant Examiner*—Joseph Murray
(74) *Attorney, Agent, or Firm*—Bryan Cave, LLP

(57) ABSTRACT

A process for the production of 2-oxo-1,3-dibenzyl-cis-4,5-imidazolidinedicarboxylic acid starting from meso-2,3-bis(benzylamino)-succinic acid dialkali metal salt is described. This process includes reacting meso-2,3-bis(benzylamino)-succinic acid dialkali metal salt with triphosgene in a two-phase solvent system consisting of an aqueous alkali hydroxide solution and an organic solvent at a temperature not exceeding about 50° C. and converting the 2-oxo-1,3-dibenzyl-cis-4,5-imidazolidinedicarboxylic acid dialkali metal salt, which results therefrom and which is present in the aqueous phase, into the desired 2-oxo-1,3-dibenzyl-cis-4,5-imidazolidinedicarboxylic acid by acidification. The product is an important intermediate in the multi-stage process for the manufacture of biotin (vitamin H).

21 Claims, No Drawings

PREPARATION OF CYCLOACID

FIELD OF THE INVENTION

The present invention relates to a process for the production of a cyclo acid, namely of 2-oxo-1,3-dibenzyl-cis-4,5-imidazolidinedicarboxylic acid, which is an important intermediate in the multi-stage process for the manufacture of biotin (vitamin H).

BACKGROUND OF THE INVENTION

The production of the aforementioned cyclo acid starting from meso-2,3-bis(benzylamino)-succinic acid in the form of its dialkali metal salt is known. Thus, for example, Seiter, U.S. Pat. No. 5,151,525 describes such a process in which phosgene is used as the reagent in an alkaline aqueous/organic two-phase solvent system for the linkage of the two secondary nitrogen atoms via a carbonyl group with resulting ring formation. In this case, anisole is employed as the essentially water-immiscible solvent for the reaction.

However, as is known, the reagent phosgene is highly toxic and, moreover, potentially explosive under the influence of other gases or certain reaction liquids, so that its use is extremely dangerous when it is carelessly handled or supervised, and special precautions are required in its transport, storage and use, e.g. the employment of safety devices in the apparatus.

SUMMARY OF THE INVENTION

An object of the present invention is to provide a process that overcomes certain of the above-referenced disadvantages for the production of 2-oxo-1,3-dibenzyl-cis-4,5-imidazolidinedicarboxylic acid starting from meso-2,3-bis(benzylamino)-succinic acid in the form of its dialkali metal salt using an alternative reagent for the ring formation. This object is achieved surprisingly well with the alternative reagent carbonic acid bis(trichloromethyl ester), also known as "bis(trichloromethyl) carbonate" or—abbreviated and referred to repeatedly hereinafter—"triphosgene," and in other respects by carrying out the process under particular reaction conditions.

One embodiment of the present invention is a process for the production of 2-oxo-1,3-dibenzyl-cis-4,5-imidazolidinedicarboxylic acid starting from meso-2,3-bis(benzylamino)-succinic acid dialkali metal salt, which process includes reacting meso-2,3-bis(benzylamino)-succinic acid dialkali metal salt with triphosgene in a two-phase solvent system consisting of an aqueous alkali hydroxide solution and an organic solvent at a temperature not exceeding about 50° C., and converting the resulting 2-oxo-1,3-dibenzyl-cis-4,5-imidazolidinedicarboxylic acid dialkali metal salt, which is present in the aqueous phase, into the desired 2-oxo-1,3-dibenzyl-cis-4,5-imidazolidinedicarboxylic acid by acidification.

Another embodiment of the invention is a process for preparing 2-oxo-1,3-dibenzyl-cis-4,5-imidazolidinedicarboxylic acid. This process includes reacting an aqueous solution of meso-2,3-bis(benzylamino)-succinic acid with an alkali metal hydroxide solution to form an alkaline aqueous solution of meso-2,3-bis(benzylamino)-succinic acid dialkali metal salt. Meso-2,3-bis(benzylamino)-succinic acid dialkali metal salt is then reacted at a temperature below about 50° C. with triphosgene in a two-phase solvent system, the two-phase solvent system consisting of an aqueous phase of an aqueous alkali hydroxide solution and an organic phase of an organic solvent. The resulting 2-oxo-1,3-dibenzyl-cis-4,5-imidazolidine-dicarboxylic acid dialkali metal salt in the aqueous phase is then acidified to form 2-oxo-1,3-dibenzyl-cis-4,5-imidazolidinedicarboxylic acid.

DETAILED DESCRIPTION OF THE INVENTION

The following Reaction Scheme is a structural representation of the process in accordance with the invention:

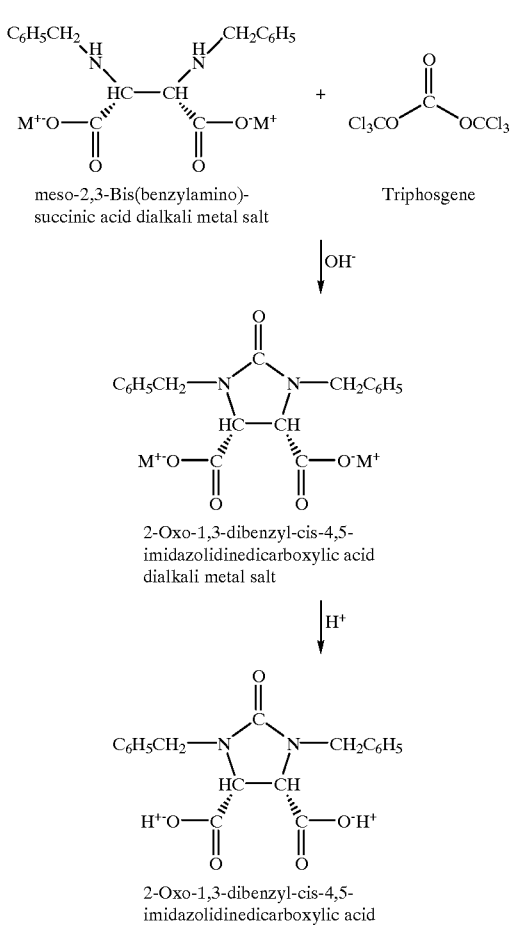

In the above Reaction Scheme, the alkali metal ion $M^+$ is either the sodium ion or the potassium ion, preferably the potassium ion, so that the disodium or dipotassium salt, preferably the latter, is used as the starting material for the process in accordance with the invention.

The triphosgene used in the present process is a white, crystalline product in the pure state with a melting point of 78° C.–80° C. It may be distilled without decomposition at a boiling point of 203° C. to 206° C. under atmospheric pressure (760 mm Hg/0.1013 MPa). Its decomposition temperature is above 350° C. Triphosgene decomposes only slowly in air and may therefore be significantly safer to handle than phosgene in air. As is known, triphosgene may be produced in good yield and quality by the photochlorination of dimethyl carbonate and has also been commercially available in large amounts for many years.

For the production of the meso-2,3-bis(benzylamino)-succinic acid dialkali metal salt, the acid itself is suspended in water, preferably deionized water, and the resulting suspension is treated with an alkali metal hydroxide solution, i.e. sodium or potassium hydroxide solution, preferably potassium hydroxide solution, generally at a pH value of about 9 to about 14, preferably at a pH value of about 12 to about 13. Such a treatment yields a clear, alkaline aqueous solution of the desired dialkali metal salt. Suitable amounts of water and added alkali metal hydroxide solution are used to ensure that the concentration of the meso-2,3-bis-(benzylamino)-succinic acid dialkali metal salt formed amounts to about 5 to about 20 weight percent, preferably about 10 to about 15 weight percent, based on the total weight of the resulting clear alkaline aqueous solution at a pH of about 9 to about 14. The concentration of the added alkali metal hydroxide solution is not critical, although it amounts to about 45–50 weight percent when commercial alkali metal hydroxide solution, e.g. potassium hydroxide solution, is used.

In the present invention, the two-phase solvent system consisting of aqueous alkali metal hydroxide solution and an organic solvent, in which the meso-2,3-bis(benzylamino)-succinic acid dialkali metal salt and the triphosgene are reacted with one another, is formed by combining the above-described clear alkaline aqueous solution of the first reaction participant with a solution of the triphosgene in the organic solvent. An aprotic organic solvent may be used as the organic solvent. Representative, non-limiting examples of aprotic organic solvents that may be used in the present invention include an aliphatic or cyclic ether, e.g. diethyl ether or, respectively, tetrahydrofuran or dioxan; an aliphatic or alicyclic hydrocarbon, e.g. hexane, octane or cyclohexane; an aliphatic or cyclic ester, e.g. ethyl acetate or γ-butyrolactone; or an aromatic hydrocarbon, e.g. benzene or toluene. Tetrahydrofuran or toluene is preferably used as the organic solvent. The concentration of the solution of the triphosgene in the solvent may vary, its upper limit depending, of course, on the employed solvent. The concentration of the triphosgene is, however, not critical, although on ecological and economical grounds it is preferably as high as possible.

In the combination of the alkaline aqueous solution of the meso-2,3-bis(benzylamino)-succinic acid dialkali metal salt with the solution of the triphosgene in the organic solvent (the "reaction participants"), the former solution is heated to an elevated temperature in the range of about 30° C. to about 50° C., preferably in the temperature range of about 40° C. to about 45° C. prior to the combination. If desired, the solution of the triphosgene may also be heated to the corresponding temperature prior to the combination. The heating may also be effected for the first time during the course of the combination or thereafter.

The sequence of combining the reaction participants is not critical, i.e. the solution of the triphosgene may be added to the alkaline aqueous solution of the meso-2,3-bis (benzylamino)-succinic acid dialkali metal salt or the alkaline aqueous solution may be added to the solution of the triphosgene. The former sequence is preferably effected. In this case, it has been found to be advantageous to add the solution of the triphosgene rather slowly and continuously, e.g. dropwise. In order to achieve a good intermixing during the combination, the mixture is suitably stirred or otherwise intermixed.

With respect to the relative amounts of meso-2,3-bis (benzylamino)-succinic acid dialkali metal salt and triphosgene after completion of the combination, the molar ratio of triphosgene:meso-2,3-bis(benzylamino)-succinic acid dialkali metal salt is about 0.33:1 to about 10:1, preferably about 1.5:1 to about 5:1. The range of about 2:1 to about 4:1 is especially preferred.

During the reaction of the triphosgene with the meso-2,3-bis(benzylamino)-succinic acid dialkali metal salt in the two-phase solvent system, the pH value of the aqueous phase is held in the range of about 8.5 to about 13, preferably in the range of about 9.5 to about 10.5. In order to maintain this pH range, aqueous sodium or potassium hydroxide solution is added as required simultaneously with the combination of the reaction participants or after completion of the combination. The concentration of the sodium or potassium hydroxide solution is not critical, although it amounts to about 5 to about 50 weight percent. It is especially preferred to use the same sodium or potassium hydroxide solution as that used for the production of the meso-2,3-bis (benzylamino)-succinic acid dialkali metal salt.

The reaction is effected at a temperature that does not exceed about 50° C., generally at temperatures in the range of about 30° C. to about 50° C., preferably at temperatures of about 40° C. to about 45° C. The pressure is not critical; the reaction is normally carried out under atmospheric or slightly elevated pressure.

If desired, the process in accordance with the invention may be effected under an inert gas atmosphere. When an inert gas atmosphere is used, nitrogen or argon is especially suitable as the inert gas, nitrogen being preferred on an industrial scale.

After the addition (i.e., combination of the reaction participants) has been effected, which usually takes about 2 to 4 hours, the reaction is normally complete. The resulting two-phase mixture may then be worked up. The desired product, 2-oxo-1,3-dibenzyl-cis-4,5-imidazolidinedicarboxylic acid in the form of its dialkali metal salt, is present mainly in the aqueous phase and is precipitated in the form of the free acid by acidification of this phase. Optionally, the previously separated aqueous phase or the entire two-phase mixture may be acidified. In the latter case, the resulting dicarboxylic acid migrates into the organic phase and must be isolated therefrom. The acid used in the acidification is mineral acid, preferably hydrochloric acid, hydrobromic acid, or sulfuric acid, of which hydrochloric acid is the most preferred mineral acid. The respective concentration and amount of the acid is selected so that the aqueous phase from which the product precipitates has a final pH value of about 0.5 to about 1.0. This ensures a good precipitation of the product. The sequence of the addition of the acid is also optional.

Where the aqueous phase has previously been separated from the organic phase, isolation of the product may be effected in any conventional manner, such as for example, by separation of the lower (heavier) aqueous phase in a separating funnel, decantation or centrifugation. Alternatively, the product is isolated from the organic phase after separation of the acidified aqueous phase, which may also be carried out by any conventional method. For example, the product may be isolated from the organic solvent by distillation.

The thus-isolated 2-oxo-1,3-dibenzyl-cis-4,5-imidazolidinedicarboxylic acid may be washed with e.g., water, dried and, if desired, purified further.

The following examples are provided to further illustrate the process of the present invention. These examples are illustrative only and are not intended to limit the scope of the invention in any way.

EXAMPLES

Example 1

16.4 g (50 mmol) of meso-2,3-bis(benzylamino)-succinic acid (DBA; about 99% pure according to HPLC) were suspended in 160 ml of deionized water under an inert gas with stirring in a five-necked sulphonation flask fitted with a Dimroth condenser, 250 ml dropping funnel with pressure balance, thermometer, mechanical stirrer, and pH electrode. 12.0 ml of 48 wt % potassium hydroxide solution (152.4 mmol KOH) were added in the above-described solution while stirring. The resulting clear solution was warmed to an internal temperature of 40° C.–45° C. in an oil bath. The DBA passed into solution as the dipotassium salt with a slightly yellowish-brown color. The solution had a pH value of 13.

44.5 g (150 mmol) of triphosgene (98% pure according to HPLC) were dissolved in 120 ml of absolute tetrahydrofuran (THF) in a 250 ml dropping funnel having a pressure balance. In so doing, no heating or gas evolution was observed. About 150 ml of triphosgene/THF solution were obtained.

The latter solution was added dropwise to the solution of the DBA dipotassium salt within 2.5 hours with vigorous stirring at an internal temperature of 40° C. to 45° C. Subsequently, the mixture was neutralized at a pH value between 9.8 and 10.3 with 48 wt % potassium hydroxide solution using a Dosimat and pH controller. The temperature was held at between 40° C. and 45° C. with a water bath. After the addition of about 100 ml of triphosgene/THF solution, the reaction mixture was observed as a slightly brown colored emulsion. Then, an additional 20 ml of deionized water were added. The entire amount of triphosgene/THF solution had been added dropwise after about 2.5 hours.

For the neutralization, 140 ml of 48 wt % potassium hydroxide solution (1.788 mol KOH) were added. The mixture was stirred for a further 5 minutes, during which time the pH of the solution remained at 10.

70 ml of deionized water were added to the solution in order to improve the separation of the aqueous phase from the organic phase. After brief stirring, the solution was transferred into a 1000 ml separating funnel. Two phases were obtained: the upper phase (58 g) contained the major part of the THF, as well as dark brown colored, water-insoluble impurities, and after concentration under reduced pressure about 0.4 g of a solid, brown mass remained behind. The lower, aqueous phase contained 2-oxo-1,3-dibenzyl-cis-4,5-imidazolidinedicarboxylic acid (CAC) and DBA as the dissolved dipotassium salt, as well as further dissolved THF. This THF had to be distilled off prior to the working up. The aqueous phase was again transferred from the separating funnel into the apparatus. The apparatus was fitted with a rising distillation bridge and the dissolved THF was distilled off up to a head temperature of 75° C. at an oil bath temperature of 85° C. to 90° C. About 33 g of distillate were obtained. The amount of reaction solution remaining amounted to 510 g or 470 ml.

For the working up, the reaction solution was acidified to a pH of 0.90 with 65 ml of 36% hydrochloric acid (754 mmol HCl) at about 40° C. while stirring well for about 2 hours. The CAC, as well as unreacted DBA separated first as a gum-like precipitate, which became fine grained after stirring at 40° C. for about 30 minutes. Thereafter, the mixture was stirred in an ice bath for a further 30 minutes, filtered through a P4 internal glass frit and the frit residue was washed neutral with 340 ml of deionized water. The residue was dried to a constant weight in a drying oven under a high vacuum and at 80° C. and thereafter taken up in 150 ml of absolute acetone. The mixture was refluxed for 30 minutes and then filtered through the same frit as previously used and washed three times on the frit with 30 ml of absolute acetone each time. The CAC was present in the yellow-brown colored acetone extracts; small amounts of DBA were detected on the frit. The acetone extracts were concentrated under reduced pressure at a bath temperature of 45° C. and a pressure of about 110 mbar (11 kPa) and thereafter dried to constant weight in a drying oven under a high vacuum at 50° C. 17.0 g of pure CAC were obtained (96% yield). 0.12 g (0.7%) of DBA was isolated from the frit. The results of the work up are presented below in Table 1:

TABLE 1

| Results | |
|---|---|
| Isolated DBA | 0.12 g = 0.7% of theory |
| Crude CAC | 17.0 g = 96% of theory |
| Content of pure CAC | 93.65% (according to HPLC) |
| Yield of pure CAC | 90.0% of theory |
| Appearance | Slightly yellow-brown, amorphous powder |
| Odor | Faint, not definable |
| Brown byproduct isolated from the THF phase | 0.4 g = 2.5% based on DBA; discarded |
| Amount of recovered THF (the THF phase contained 57.5 g of THF. The amount of distillate was 33.0 g of THF) | 90.5% g = 85% of theory |
| Amount of potassium chloride in the aqueous filtrate (corresponding to the neutralization of 1.930 mol of KOH with HCl) | 144 g |

A maximum of 1% of DBA, as well as 2–3% of unknown byproducts, were still present in the aqueous filtrate according to analysis by thin-layer chromatography (TLC). No CAC was present in the filtrate. The filtrate was discarded.

Analysis

CAC and DBA may be determined well by HPLC. CAC, DBA, as well as the brown byproducts, may be detected qualitatively by means of TLC. The following Rf values were determined using Merck Kieselgel 60 $F_{254}$ TLC plates, 50 toluene/50 glacial acetic acid/10 methanol (parts by volume in each case) as the eluant mixture and acetone as the solvent for the CAC and the brown byproducts and dilute hydrochloric acid as the solvent for the DBA:

| BA | 0.38 |
|---|---|
| AC | 0.51 |
| Byproducts | 0.84 spread |

The elution time was 45–50 minutes and the development was effected in about 2 hours in an iodine tank, which gave brown flecks.

In summary, the DBA was converted almost completely into CAC with 3 equivalents of triphosgene dissolved in THF. The content of pure CAC amounted to 93.6% and the yield of pure CAC amounted to 90%.

Example 2

16.6 g of DBA (98–99%; 50 mmol DBA 100%) were weighed into the prepared apparatus and suspended in 115 ml of deionized water. The contents of the flask were heated to 45° C. in an oil bath, and then 10.0 ml of potassium hydroxide solution (48 wt %, 127 mmol) were added. After stirring for 10 minutes, the DBA dissolved to give a clear solution. The pH of the solution was 12.4. The solution was neutralized to pH 9.9 with 0.5 ml of concentrated hydrochloric acid (6 mmol).

29.7 g of triphosgene (100 mmol) were weighed into a 250 ml dropping funnel and dissolved in 76 ml of absolute toluene. This solution was added dropwise, while stirring well for about one hour and 45 minutes at 45° C., to the solution of the DBA dipotassium salt at pH 9.5 to 10.5. A brown emulsion was obtained. This was neutralized with 92 ml of 48 wt % potassium hydroxide solution (1.168 mol KOH). The pH value amounted to 9.9. Because triphosgene dissolved in toluene reacts less rapidly with aqueous solutions, the mixture was stirred for a further 30 minutes. In so doing, the pH value fell to 9.7. The mixture was neutralized to pH 9.9 with 2.0 ml of 48 wt % potassium hydroxide solution (25.4 mmol KOH). The pH value remained constant at pH 9.94. This signified that all of the triphosgene had reacted. The total time required for the conversion of DBA into CAC amounted to about 2.5 hours.

Thereafter, the contents of the flask were transferred as completely as possible into a 1000 ml separating funnel. A good phase separation was obtained very rapidly. The impurities were present in the upper, dark brown colored toluene phase. The amount of this phase was 62.6 g. The lower, slightly yellow colored phase contained the alkaline aqueous reaction solution. The volume amounted to about 300 ml. This solution was transferred into a 500 ml dropping funnel.

For the working up (direct precipitation), 45 ml of concentrated hydrochloric acid (36 wt %; 522 mmol) were placed in a 750 ml four-necked sulphonation flask fitted with a mechanical stirrer, thermometer, and pH electrode. About 20 mg of crude CAC were added for seeding and the mixture was then heated to about 40° C. in an oil bath. Thereafter, the alkaline aqueous reaction solution was added dropwise by means of a dropping funnel to the concentrated hydrochloric acid while stirring vigorously. CAC crystals formed with the evolution of $CO_2$ already after the addition of about 20 ml of this reaction solution. The velocity of the dropwise addition was adjusted to 5 ml/minute. All of the alkaline aqueous reaction solution had been added dropwise after 30 minutes.

Crude CAC formed a fine crystalline precipitate. It was stirred at 40° C. for 15 minutes, thereafter cooled and stirred in an ice bath at about +5° C. for a further 30 minutes. The pH value of the aqueous solution amounted to 0.64.

Thereafter, the solution was filtered through a P4 internal glass frit and the yellow-brown, crystalline residue was washed neutral three times with 40 ml of deionized water each time and dried to a constant weight in a drying oven under a high vacuum at 80° C. The results of this work up are presented in Table 2 below:

TABLE 2

| Results | |
|---|---|
| Crude CAC | 16.7 g = 94.35% of theory |
| Content of pure CAC | 94.1% (according to HPLC) |
| Yield of pure CAC | 88% of theory |

The amount of the toluene phase was 62.6 g. After concentration under reduced pressure, about 0.7 g of brown, non-definable byproducts remained. This corresponded to 4.2% based on the amount of DBA used. 60 g of toluene distillate were obtained; this corresponded to about 69 ml of toluene or 90% of the amount of toluene solvent used (76 ml).

1.193 mol of potassium chloride were present in the aqueous filtrate. This corresponded to an amount of salt of 88.94 g of potassium chloride. Moreover, according to TLC, this filtrate still contained small amounts of CAC (max. 0.5–1%), DBA (max. 1%) as well as byproducts (about 2%) which were not investigated in more detail. The aqueous filtrate was discarded.

The invention being thus described, it will be obvious that the same may be varied in many ways. Such variations are not to be regarded as a departure from the spirit and scope of the invention and all such modifications are intended to be included within the scope of the following claims.

What is claimed is:

1. A process for producing 2-oxo-1,3-dibenzyl-cis-4,5-imidazolidinedicarboxylic acid comprising:

(a) reacting meso-2,3-bis(benzylamino)-succinic acid dialkali metal salt with triphosgene in a two-phase solvent system consisting of an aqueous phase of an aqueous alkali hydroxide solution and an organic phase of an organic solvent at a temperature below about 50° C.; and (b) acidifying the resulting 2-oxo-1,3-dibenzyl-cis-4,5-imidazolidinedicarboxylic acid dialkali metal salt in the aqueous phase to form 2-oxo-1,3-dibenzyl-cis-4,5-imidazolidinedicarboxylic acid.

2. A process according to claim 1 wherein the meso-2,3-bis(benzylamino)-succinic acid dialkali metal salt is meso-2,3-bis(benzylamino)-succinic acid disodium salt or meso-2,3-bis(benzylamino)-succinic acid dipotassium salt.

3. A process according to claim 2 wherein the meso-2,3-bis(benzylamino)-succinic acid dialkali metal salt is meso-2,3-bis(benzylamino)-succinic acid dipotassium salt.

4. A process according to claim 1 wherein the meso-2,3-bis(benzylamino)-succinic acid dialkali metal salt is prepared by reacting an aqueous suspension of meso-2,3-bis(benzylamino)-succinic acid with an alkali metal hydroxide solution.

5. A process according to claim 4 wherein the alkali metal hydroxide solution is a potassium hydroxide solution.

6. A process according to claim 4 wherein the concentration of the meso-2,3-bis(benzylamino)-succinic acid dialkali metal salt is about 5 wt % to about 20 wt % based on the total weight of the solution at a pH of about 9 to about 14.

7. A process according to claim 6 wherein the concentration of the meso-2,3-bis(benzylamino)-succinic acid dialkali metal salt is about 10 wt % to about 15 wt % based on the total weight of the solution at a pH of about 9 to about 14.

8. A process according to claim 1 wherein the organic solvent is an aprotic organic solvent.

9. A process according to claim 8 wherein the aprotic organic solvent is selected from the group consisting of aliphatic ethers, cyclic ethers, aliphatic hydrocarbons, alicyclic hydrocarbons, aliphatic esters, cyclic esters, and aromatic hydrocarbons.

10. A process according to claim 9 wherein the aprotic organic solvent is selected from the group consisting of diethyl ether, tetrahydrofuran, dioxan, hexane, octane, cyclohexane, ethyl acetate, γ-butyrolactone, benzene, and toluene.

11. A process according to claim 10 wherein the aprotic organic solvent is tetrahydrofuran.

12. A process according to claim 10 wherein the aprotic organic solvent is toluene.

13. A process according to claim 1 wherein the alkaline aqueous solution of the meso-2,3-bis(benzylamino)-succinic acid dialkali metal salt, the solution of the triphosgene in the organic solvent, or both are heated to about 30° C. to about 50° C.

14. A process according to claim 13 wherein the alkaline aqueous solution of the meso-2,3-bis(benzylamino)-succinic acid dialkali metal salt, the solution of the triphosgene in the organic solvent, or both are heated to about 40° C. to about 50° C.

15. A process according to claim 1 wherein the molar ratio of triphosgene:meso-2,3-bis(benzylamine)-succinic acid dialkali metal salt is about 0.33:1 to about 10:1.

16. A process according to claim 15 wherein the molar ratio of triphosgene:meso-2,3-bis(benzylamine)-succinic acid dialkali metal salt is about 1.5:1 to 5:1.

17. A process according to claim 16 wherein the molar ratio of triphosgene:meso-2,3-bis(benzylamine)-succinic acid dialkali metal salt is about 2:1 to about 4:1.

18. A process according to claim 1 wherein the pH of the aqueous phase in the two-phase solvent system is about 8.5 to about 13.

19. A process according to claim 18 wherein the pH of the aqueous phase in the two-phase solvent system is about 9.5 to about 10.5.

20. A process according to claim 1 wherein acidifying the 2-oxo-1,3-dibenzyl-cis-4,5-imidazolidinedicarboxylic acid dialkali metal salt is carried out with a mineral acid.

21. A process according to claim 20 wherein the mineral acid is selected from the group consisting of hydrochloric acid, hydrobromic acid, and sulfuric acid.

\* \* \* \* \*